(12) United States Patent
Estivill Palleja et al.

(10) Patent No.: US 6,251,664 B1
(45) Date of Patent: Jun. 26, 2001

(54) HUMAN GENE SEQUENCE OF THE DOWN SYNDROME CRITICAL REGION OF HUMAN CHROMOSOME 21, CODING FOR A SERINE-THREONINE PROTEIN KINASE (MNB), EXPRESSED IN THE NEURONAL REGIONS AFFECTED IN DOWN SYNDROME

(75) Inventors: Xavier Estivill Palleja, Instituto de Investigación Oncológica Autovía de Castelldefells, Km. 2, 7, l'Hospitalet de Llobregat; Melanie Pritchard; Jordi Guimera Vilaro, all of Barcelona (ES)

(73) Assignee: Xavier Estivill Palleja, Barcelona (ES)

( * ) Notice: Subject to any disclaimer, the term of this patent is extended or adjusted under 35 U.S.C. 154(b) by 0 days.

(21) Appl. No.: 08/789,275

(22) Filed: Jan. 28, 1997

(51) Int. Cl.[7] .......................... C12N 15/52; C12N 15/63; C12N 15/85
(52) U.S. Cl. ................. 435/325; 435/252.3; 435/320.1; 536/23.5
(58) Field of Search ................................ 536/23.1, 23.5; 435/325, 252.3, 320.1

(56) References Cited

U.S. PATENT DOCUMENTS 5,874,230 * 2/1999 Song et al. ........................ 435/7.8

OTHER PUBLICATIONS

Song et al. Genomics 38: 331–339, 1996.*
Shindoh et al. Biochem Biophys. Res. Comm. 225:92–99, 1996.*
Guimera et al. Human Molecular Genetics 5:1305–1310, 1996.*
Kentrup et al. J. Biol. Chem. 271: 3488–3495, 1996. admitted prior art.*
Rudinger, In "Peptide Hormones" (ed. J.A. Parsons) University Park Press, Baltimore, pp. 1–7, 1976.*

* cited by examiner

*Primary Examiner*—Gary L. Kunz
*Assistant Examiner*—Robert C. Hayes
(74) *Attorney, Agent, or Firm*—Ladas and Parry

(57) ABSTRACT

An isolated human Down Syndrome critical region (MNB) DNA sequence having the nucleotide sequence depicted in SEQ ID NO:1; vector including the human Down Syndrome critical region (MNB) sequence; and isolated host cells containing the vector are provided.

3 Claims, 3 Drawing Sheets

FIG. 1

HUMAN GENE SEQUENCE OF THE DOWN SYNDROME CRITICAL REGION OF HUMAN CHROMOSOME 21, CODING FOR A SERINE-THREONINE PROTEIN KINASE (MNB), EXPRESSED IN THE NEURONAL REGIONS AFFECTED IN DOWN SYNDROME

FIELD OF THE INVENTION

The minibrain (mnb) gene of *Drosophila melanoaster* encodes a serine-threonine protein kinase with an essential role in post-embryonic neurogenesis. A corresponding human gene with similar function to mnb could provide important. insights into both normal brain development and the abnormal. brain development and mental retardation observed in many congenital disorders. Trisomy 21 or Down syndrome (DS) is the most frequent human birth defect. It is associated with mental retardation and a broad spectrum of physical abnormalities. A region on human chromosome 21 has been designated the Down syndrome critical region (DSCR) and when present in three copies, this is responsible for many of the characteristic features of DS, including mental retardation. We have isolated a human homologue of mnb from the DSCR. Using a human probe of MNB, expression was detected in situ in several regions of the mouse brain, including the olfactory bulb, the cerebellum, the cerebral cortex, the pyramidal cell layer of the hippocampus and several hypothalamic nuclei. This expression pattern corresponds to the regions of the brain that are abnormal in individuals with DS and suggests that overexpression of MNB could have detrimental consequences in DS patients.

PRIOR ART

Down syndrome (DS) is one of the most frequent congenital defects. There is a broad spectrum of physical abnormalities associated with the syndrome, including anomalies of the gastrointestinal tract, increased risk of leukemia, defects of the immune and endocrine systems, early onset of Alzheimer's dementia and distinct facial and physical features, but perhaps the most debilitating is a rather severe mental retardation. In most cases DS is due to three full copies of human chromosome 21 which arise primarily during maternal non-disjunction, but occasionally DS occurs in people carrying unbalanced translocations, which result in the triplication of only a part of chromosome 21. By correlating phenotype with genotype in patients with partial trisomies a region has been defined, named the DSCR (Down syndrome critical region) which, when present in three copies, is responsible for many of the characteristic features of DS including mental retardation (1).

The phenotypic consequences of DS presumably result from the overexpression and subsequent interactions of a subset of chromosome 21 genes and the future challenge is to correlate overexpression of these genes, singly or in combination, with the presence of the DS phenotype. The first step is to identify the genes in the DSCR and then assess their potential contributions to the pathophysiology of DS. Assigning a function to a gene, particularly in humans, is not simple. Investigators rely on finding clues to function by analyzing the expression pattern of a gene, by looking for protein domains or motifs with known functions or by extrapolating from another species in which the function of the homologous gene is known.

The deduced amino acid sequence of MNB cDNA exhibits structural features which are shared with Dyrk (the rat homologue of mnb). The core domains which contain amino acids found in the catalytic sites of protein kinases are identical with the exception of two residues and both proteins have a potential nuclear translocation signal (FIG. 1).

Any gene with a role in early neurogenesis is potentially important with respect to the abnormal brain development and mental retardation seen in DS. Genes which show temporal or high levels of expression during the development of the central nervous system may be of special importance in DS, especially in the pathogenesis of mental retardation. In Drosophila, the mnb gene appears to play an essential role during post-embryonic neurogenesis in regulating the numbers of distinct types of neuronal cells (2). Mutant mnb flies are characterized by a marked size reduction of the adult optic lobes and the central brain hemispheres. This is caused by the abnormal spacing of neuroblasts and hence a reduction in the production of neuronal progeny. The mnb gene encodes a serine-threonine protein kinase which is expressed in distinct neuroblast proliferation centers during Drosophila post-embryonic neurogenesis. We have isolated a human homologue of mnb from the DSCR and we show, by in situ RNA hybridization studies in mouse brains, that Mhb is normally expressed in regions of the brain which are abnormal in individuals with DS. The minibrain kinases (mnb, MNB, and Dyrk) share sequence similarity with the cyclin-dependent kinases, which are known to regulate cellular proliferation, suggesting a role for mnb in the correct mitosis of neuroblast progeny (2). Although the overall scheme of neuronal development is quite different in invertebrates and vertebrates, molecular studies on vertebrate neurogenesis have revealed a remarkable evolutionary conservation of the cellular mechanisms of neuronal development. Moreover, cyclin-dependent kinases are known to regulate cellular proliferation in various species, suggesting a more universal regulatory mechanism. It is conceivable that MNB has a role in the processes which generate neuronal cells in the brain during post-embryonic development.

The detection of MNB in the DSCR on chromosome 21 suggests that it may be involved in the altered neuronal development observed in DS. Although in Drosophila the mnb phenotype was due to a reduction in the level of expression of the mnb gene, we expect that in DS, MNB is overexpressed. At a gross morphological level, DS brains are smaller than normal and there is a decrease in the number of neurons. Neuronal number is reduced in distinct regions, including the cochlear nuclei, cerebellum, hippocampus, the cholinergic neurons of the basal forebrain, the granular layers of the cerebral cortex, and in areas of the brain stem. These abnormalities occur in regions where the Mnb gene is normally expressed and are consistent with the view that altered expression is in some way detrimental.

It is presumed that the structural alterations observed in the brain, together with the accompanying functional changes may account for the subsequent physiological and cognitive abnormalities associated with DS. Therefore, it is likely that genes involved in neurogenesis and which have altered expression in DS might account, at least partly, for the alterations that lead to mental retardation. The location of MNB in the DSCR together with its probable function in neurogenesis, supports MNB as a strong candidate gene to produce some of the neurological abnormalities present in DS patients. With the help of neuropathological, neurochemical and behavioral studies in transgenic animals, we may be able to dissect the components contributing to the mental retardation and to the complexity of the DS phenotype.

SUMMARY OF THE INVENTION

We have isolated a new human gene sequence, MNB, located in the 21q22.2 region. The expression of MNB was evident in the olfactory bulb, the cerebellum, the cerebral cortex, the pyramidal cell layer of the hippocampus and several hypothalamic nuclei, coding for a serine-threonine protein kinase. The overexpression of MNB may be involved in pathogenic abnormalities of mental retardation and/or other defects in patients with Down syndrome.

DETAILED DESCRIPTION OF THE INVENTION

Isolation of a mnb Homologue

In preparation for isolating human chromosome 21 expressed sequences we constructed contiguous cosmid sub-libraries from YACs from various regions of chromosome 21, including YACs from the DSCR. Pools of these cosmids were used for the isolation of partial cDNAs by direct selection (3) and for exon trapping experiments (4, 5). A total of 576 clones were isolated and arrayed. Of these 576 selected clones, 107 mapped back to human chromosome 21. In total we have 41 non-redundant putative cDNAs, of which 24 are novel, i.e. do not match known genes or ESTs in the databases (manuscript in preparation). We have isolated two known chromosome 21 genes, DSC1 and GIRK2 and another 13 partial cDNAs have significant matches with entries in the databases. Using the blastx program, two non-overlapping partial cDNAs (D7-X4 and D1-34) showed significant similarity to a Drosophila melanogaster serine/threonine kinase (accession no. X70794) (D7-X4 P(N)= 3.0e$^{-18}$; D1-34 P(N)=2.5e$^{-36}$). This serine/threonine kinase is the product of the Drosophila minibrain (mnb) gene. Using the blasting program, D1-34, D7-X4 and a third partial cDNA (D2-34) had almost complete sequence identity (P(N)=5.3e$^{-60}$ for D1-34) with the Dyrk (Dual specificity Yak1-related kinase) mRNA from Rat norvegicus (accession no. X79769). In addition, D2-34 also matched a previously mapped chromosome 21 EST (L25452) and a mouse EST (Z31282). Using the partial cDNAs as probes, we subsequently isolated five overlapping clones from a human fetal brain library (Clontech). The combined-sequence of these cDNAs spanned 2373 bp and included a complete coding region of 763 amino acids. We have designated the new gene MNB, SEQ ID NO:1 human homologue of mnb. FIG. 1 shows an alignment of the amino acid sequences of MNB, mnb and Dyrk.

Mapping of MNB

Southern blot analysis of total human genomic DNA digested with EcoRI and TaqI showed a single band when hybridized with probe D2-34. Therefore, MNB is a single copy gene. Hybrid cell line DNA, containing human chromosome 21 as its only human component, showed the same bands when probed with D2-34 but with an additional mouse band. The partial cDNAs (D7-X4 from exon trapping, D1-34 and D2-34 from cDNA selection) were mapped by hybridization to the chromosome 21 YAC 336G11 and to cosmids shown in FIG. 2. YAC 336G11 was shown by FISH to be non chimaeric. This places the MNB gene within the proximal half of the DSCR (21q22.2), between D21S17 and D21S55. MNB spans the cosmid containing marker D21S270, is approximately 200 kb from marker D21S55 and is proximal to marker D21S337.

Expression of Minibrain

Northern blot analysis using D1-34 as a probe identified one transcript of 6.1 kb in human fetal brain, liver, lung and kidney (FIG. 3a). There was no evidence of smaller transcripts in the human tissues with a prolonged exposure of the autoradiograph. In mouse there were two major transcripts of 6.1 kb and 3.1 kb (FIG. 3b), similar to the results of Kentrup et al. in rat (6). RNA in situ hybridization studies of mouse brains were carried out using a 40-mer antisense oligonucleotide derived from cDNA D1-34. Expression of Mnb was evident in the olfactory bulb, the cerebellum, the cerebral cortex, the pyramidal cell layer of the hippocampus and several hypothalamic nuclei (FIG. 4).

During the course of this work Kentrup and co-workers published the identification and functional studies of Dyrk. They speculated that Dyrk is involved in cell cycle control and is the rat homologue of mnb (6). Futhermore, based on the high similarity of Dyrk with the human EST (L25452), Kentrup et al suggested that the human homologue of Dyrk maps to 21q22.2. This human homologue of Dyrk is MNB. Human MNB is expressed as a 6.1 kb transcript and there is no evidence of a smaller transcript analogous to the 3.1 kb transcript found in rat and mouse. The Drosophila mnb gene encodes three alternatively spliced transcripts (5.5, 4.4 and 4.2 kb) (2). It is unknown whether the two transcripts observed in rodents are alternative splicing products. The deduced amino acid sequence of our partial MNB CDNA exhibits structural features which are shared with Dyrk. The core domains which contain amino acids found in the catalytic sites of protein kinases are identical with the exception of two residues and both proteins have a. potential nuclear translocation signal (FIG. 1).

Methodology Used in the Implementation of the Invention

YACs and Cosmids

Selected human chromosome 21 YACs were tested for chimaerism by FISH. YACs were grown on AHC selective medium and were encapsulated in agarose beads. Total yeast DNA containing YACs was partially digested with MboI and ligated into the BamHI site of SuperCos (Stratagene). Cosmids were packaged using Stratagene Gigapack II Plus packaging extracts. Clones containing human inserts were identified by screening with a radiolabelled total human DNA probe. Cosmid contigs were generated using riboprobe and linear PCR strategies.

Probes and Hybridization

Probes were labeled with [a$^{32}$P] dCTP by random priming. Colony and plaque hybridizations were in 7% SDS/0.5 M sodium phosphate buffer (pH 7.0). CDNA probes were hybridized to filters containing the hybrid cell line WAV17, containing human chromosome 21 as its only human component.

cDNA Selection and Exon Trapping

A pool of 502 cosmid DNAs from the libraries made from seven human chromosome 21 YACs was used for cDNA selection, essentially as described (3). The cDNA source was human fetal brain mRNA which had been reverse transcribed using random hexamers and oligo dT. Linkers were ligated and these cDNAs were then hybridized with the pool of biotinylated cosmids. The selected cDNAs were amplified using the linker primer (5'-CTCGAGAATTCTGGATCCTC-3') SEQ ID NO:2 with a (CUA)$_4$ tail and subcloned in pAMP10 (GIBCO-BRL). Exon trapping was as described (4, 5) using a pool of 12 overlapping, -non-redundant cosmids from YAC 336G11 subcloned in pSPL3. Amplified exons were directionally subcloned in pAMP1 (GIBCO-BRL). Using a Biomek 1000 station (Beckman), colonies were gridded at a high density onto nylon filters. Clones were sequenced with the M13R and M13D primers using fluorescent DyeDeoxy Terminators on an ABI373A automatic DNA sequencer (Applied Biosystems).

RNA Analyses

Northern blots (Clontech) containing poly (A⁺) mRNA from human fetal tissues or adult mouse tissues were hybridized with D1-34 according to the manufacturer's protocol. RNA in situ hybridization studies on sections of mouse brain were carried out with a 40-mer antisense oligonucleotide (5'-GGAATACCCAGAACTTCCACTATTTTATTCATCTGATCTA-3') SEQ ID NO:3, essentially as described previously (25), except that following hybridization, sections were washed twice in 1×SSC (150 mM sodium chloride and 15 mM sodium citrate, pH 7.0) at 52° C. for 1 h each. A 40-mer sense oligonucleotide was used as a control under the same conditions, and gave no signals in the hybridization experiments performed.

Bibliography

1. Delabar, J. M., Théophile, D., Rahmani, Z., Chettouh, Z., Blouin, J. L., Prieur, M., Nöel, B. and Sinet, P. M. (1993) Molecular-mapping of twenty-four features of Down syndrome on chromosome 21. Eur. J. Hum. Genet., 1, 114–124.

2. Tejedor, F., Zhu, X. R., Kaltenbach, E., Ackermann, A., Baumann, A., Canal, I., Heisenberg, M., Fischbach, K. F. and Pongs, O. (1995) Minibrain: a new protein kinase family involved in post-embryonic neurogenesis in Drosophila. Neuron, 14, 287–301.

3. Lovett, M., Kere, J. and Hinton, L. M. (1991) Direct selection: A method for the selection of cDNAs encoded by large genomic regions. Proc. Natl. Acad. Sci. U.S.A., 88, 9628–9632.

4. Buckler, A. J., Chang, D. D., Graw, S. L., Brook, J. D, Haber, D. A., Sharp, P. A. and Housman D. E. (1991) Exon amplification: A strategy to isolate mammalian genes based on RNA splicing. Proc. Natl. Acad. Sci. U.S.A., 88, 4005–4009.

5. Church, D. M., Stotler, C. J., Rutter, J. L., Murrell, J. R., Trofatter, J. A. and Buckler, A. J. (1994) Isolation of genes from complex sources of mammalian genomic DNA using exon amplification. Nature Genet., 6, 98–105.

6. Kentrup, H., Becker, W., Heukelbach, J., Wilmes, A., Schuermann, A., Huppertz, C., Kainulainen, H. and Joost, H. G. (1996) Dyrk: A dual-specificity protein kinase with unique structural features whose activity is dependent on tyrosine residues between subdomains VII and VIII. J. Biol. Chem., 271, 3488–3495.

7. Fuentes J-J., Pritchard M. A., Planas A. M., Bosch A., Ferrer I. and Estivil, X. (1995) A new human gene from the Down syndrome critical region encodes a proline-rich protein highly expressed in fetal brain and heart. Hum. Mol. Genet., 4, 1935–1944.

EXPLANATION OF THE FIGURES

Figure 1:
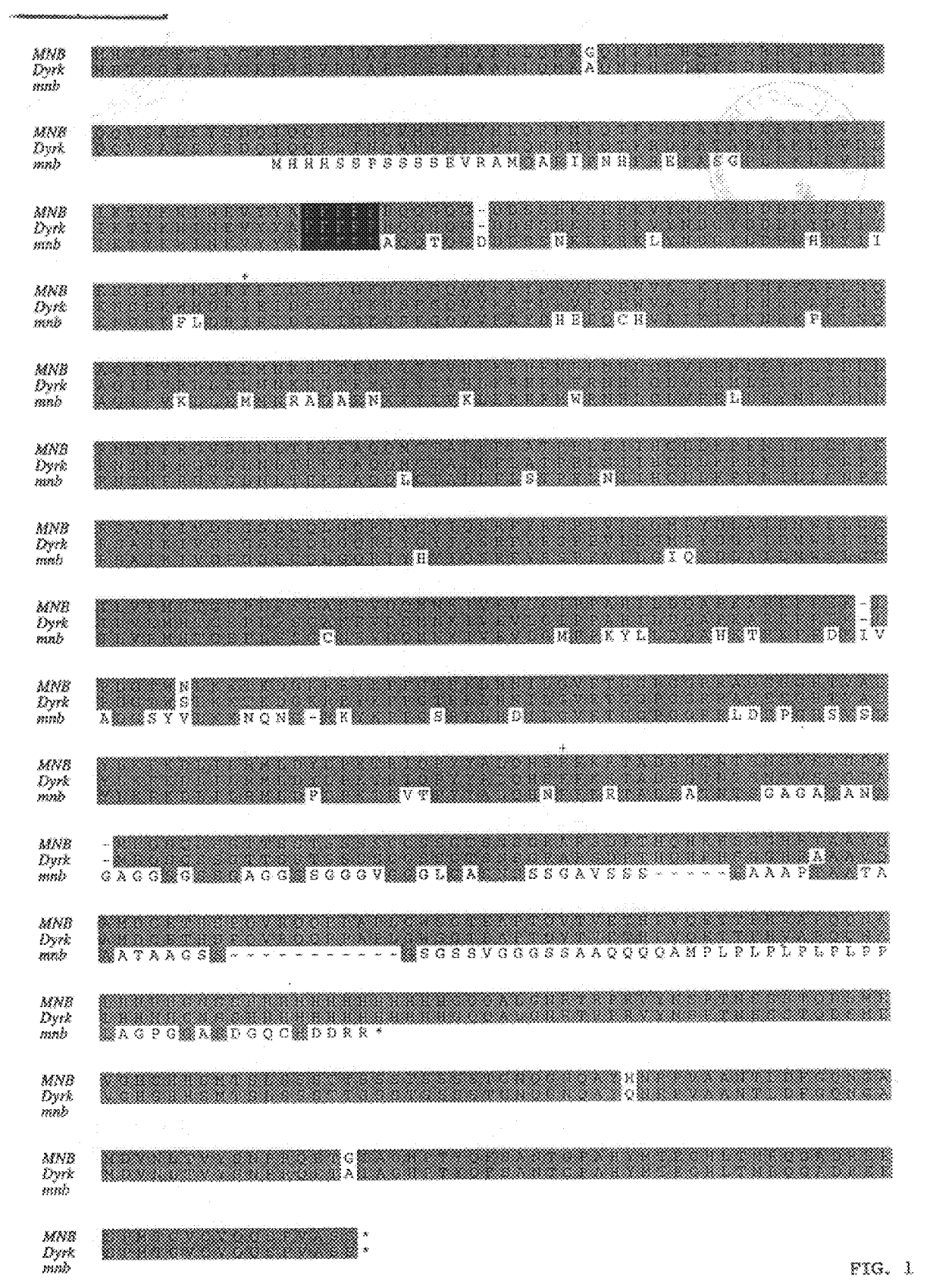

FIG. 1 Alignment of minibrain kinase sequences generated with the Wisconsin Package programs Gap, Pileup and Prettybox. Only amino acid identities are shaded. mnb is the Drosophila minibrain (accession no. X70794) SEQ ID NO:6; Dyrk is a rat minibrain homologue (accession no. X79769) SEQ ID NO:5. MNB is a human minibrain homologue from chromosome 21 (accession no. U52373) SEQ ID NO:4. The complete coding sequences of MNB, mnb and Dyrk are shown. A dash indicates spacing between amino acids to achieve best alignment. The blastx amino acid identity between the MNB sequence and Dyrk was 99% (P(N)=0.0) and between MNB and mnbwas 69% (P(N)= $3.3e^{-262}$). The core domain which contains amino acids found in the catalytic sites of protein kinases (16) lies between the plus signs. In this region there are two amino acid differences between MNB and Dyrk. A. potential nuclear translocation signal is indicated by black shading. An asterisk represents a stop codon.

SEQUENCE LISTING

<160> NUMBER OF SEQ ID NOS: 6

Figure 2:
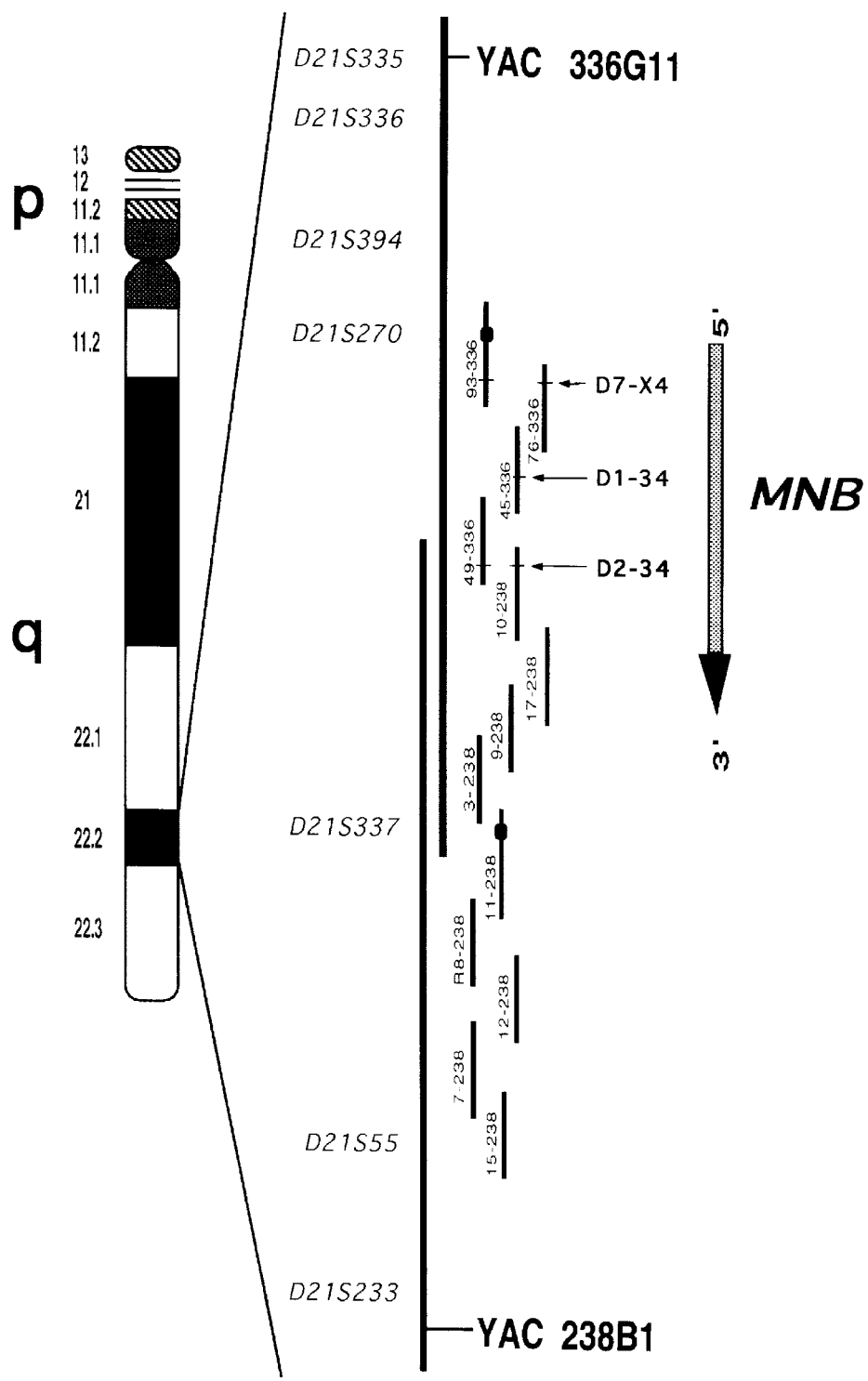
FIG. 2 Localisation of human MNB to the DSCR on human chromosome 21. Schematic representation of the 21q22.2 region, STS map and maps of YACs 336G11 and 238B1. Cosmids containing the genomic region of MNB are shown. The partial cDNAs, indicated by an arrow, are below the cosmids they map to. The direction of transcription of MNB is shown. The STS verified in the cosmids by PCR are indicated by a filled circle.
Figure 3:
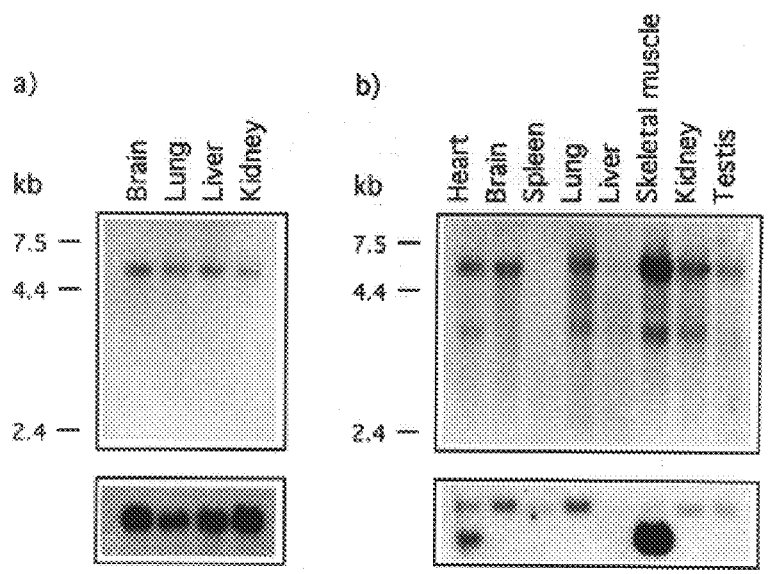
FIGS. 3A–B Northern blot analysis of MNB. Nylon membranes containing 2 mg of poly (A)⁺RNAs were hybridized with the human clone D1-34 which corresponds to MNB. a/ Northern analysis of human fetal mRNA. b/ Northern analysis of adult mouse mRNA. In mouse lung a third band of 2.5 kb was detected. The lower panel in a and b shows hybridization with a b-actin probe.
Figure 4:
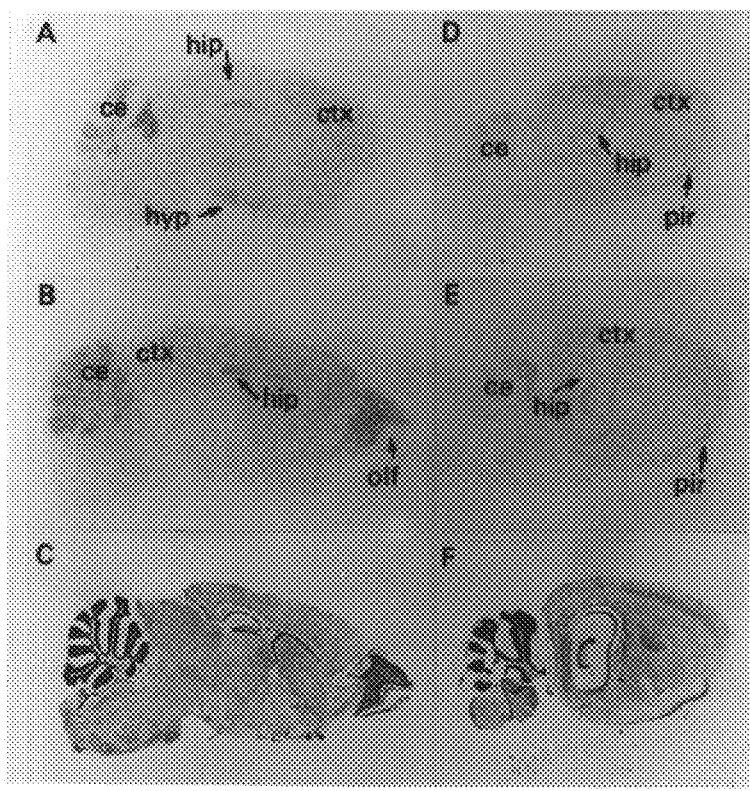
FIGS. 4A–F Expression of Mnb MRNA in the brain of the adult mouse using a 40-mer antisense probe derived from the human MNB sequence. Sagital sections of the brain are shown. C and F are the same as B and E but stained with crystal violet. Signals were evident in olfactory bulb (olf), cerebellum (ce), cortex (ctx) and piriform cortex (pir), hippocampus (hip) and hypothalamus (hyp). A 40-mer sense oligonucleotide was used as a control under the same conditions, giving no signal in the hybridization experiments performed.

<210> SEQ ID NO: 1
<211> LENGTH: 2373
<212> TYPE: DNA
<213> ORGANISM: Homo sapiens
<220> FEATURE:

<400> SEQUENCE: 1

```
gttatagttt tgccgctgga ctcttccctc ccttccccca ccccatcagg              50
atgatatgag acttgaaaga agacg atg cat aca gga gga gag act tca gca      102
                         Met His Thr Gly Gly Glu Thr Ser Ala
```

-continued

```
                              5
tgc aaa cct tca tct gtt cgg ctt gca ccg tca ttt tca ttc cat gct    150
Cys Lys Pro Ser Ser Val Arg Leu Ala Pro Ser Phe Ser Phe His Ala
 10              15                  20                  25 gct ggc ctt cag atg gct gga cag atg ccc cat tca cat cag tac agt    198
Ala Gly Leu Gln Met Ala Gly Gln Met Pro His Ser His Gln Tyr Ser
                 30                  35                  40 gac cgt cgc cag cca aac ata agt gac caa cag gtt tct gcc tta tca    246
Asp Arg Arg Gln Pro Asn Ile Ser Asp Gln Gln Val Ser Ala Leu Ser
             45                  50                  55 tat tct gac cag att cag caa cct cta act aac cag gtg atg cct gat    294
Tyr Ser Asp Gln Ile Gln Gln Pro Leu Thr Asn Gln Val Met Pro Asp
         60                  65                  70 att gtc atg tta cag agg cgg atg ccc caa acc ttc cgt gac cca gca    342
Ile Val Met Leu Gln Arg Arg Met Pro Gln Thr Phe Arg Asp Pro Ala
     75                  80                  85 act gct ccc ctg aga aaa ctt tct gtt gac ttg atc aaa aca tac aag    390
Thr Ala Pro Leu Arg Lys Leu Ser Val Asp Leu Ile Lys Thr Tyr Lys
 90                  95                 100                 105 cat att aat gag gtt tac tat gca aaa aag aag cga aga cac caa cag    438
His Ile Asn Glu Val Tyr Tyr Ala Lys Lys Lys Arg Arg His Gln Gln
                110                 115                 120 ggc cag gga gac gat tct agt cat aag aag gaa cgg aag gtt tac aat    486
Gly Gln Gly Asp Asp Ser Ser His Lys Lys Glu Arg Lys Val Tyr Asn
            125                 130                 135 gat ggt tat gat gat gat aac tat gat tat att gta aaa aac gga gaa    534
Asp Gly Tyr Asp Asp Asp Asn Tyr Asp Tyr Ile Val Lys Asn Gly Glu
        140                 145                 150 aag tgg atg gat cgt tac gaa att gac tcc ttg ata ggc aaa ggt tcc    582
Lys Trp Met Asp Arg Tyr Glu Ile Asp Ser Leu Ile Gly Lys Gly Ser
    155                 160                 165 ttt gga cag gtt gta aag gca tat gat cgt gtg gag caa gaa tgg gtt    630
Phe Gly Gln Val Val Lys Ala Tyr Asp Arg Val Glu Gln Glu Trp Val
170                 175                 180                 185 att aaa gcc ata ata aag aac aag aag gct ttt ctg aat caa gca cag    678
Ala Ile Lys Ile Ile Lys Asn Lys Lys Ala Phe Leu Asn Gln Ala Gln
                190                 195                 200 ata gaa gtg cga ctt ctt gag ctc atg aac aaa cat gac act gaa atg    726
Ile Glu Val Arg Leu Leu Glu Leu Met Asn Lys His Asp Thr Glu Met
            205                 210                 215 aaa tac tac ata gtg cat ttg aaa cgc cac ttt atg ttt cga aac cat    774
Lys Tyr Tyr Ile Val His Leu Lys Arg His Phe Met Phe Arg Asn His
        220                 225                 230 ctc tgt tta gtt ttt gaa atg ctg tcc tac aac ctc tat gac ttg ctg    822
Leu Val Phe Glu Met Leu Ser Tyr Asn Leu Tyr Asp Leu Leu Arg Leu
    235                 240                 245 aga aac acc aat ttc cga ggg gtc tct ttg aac cta aca cga aag ttt    870
Cys Asn Thr Asn Phe Arg Gly Val Ser Leu Asn Leu Thr Arg Lys Phe
250                 255                 260                 265 gcg caa cag atg tgc act gca ctg ctt ttc ctt gcg act cca gaa ctt    918
Ala Gln Gln Met Cys Thr Ala Leu Leu Phe Leu Ala Thr Pro Glu Leu
                270                 275                 280 agt atc att cac tgt gat cta aaa cct gaa aat atc ctt ctt tgt aac    966
Ser Ile Ile His Cys Asp Leu Lys Pro Glu Asn Ile Leu Leu Cys Asn
            285                 290                 295 ccc aaa cgc agt gca atc aag ata gtt gac ttt ggc agt tct tgt cag   1014
Pro Lys Arg Ser Ala Ile Lys Ile Val Asp Phe Gly Ser Ser Cys Gln
        300                 305                 310 ttg ggg cag agg ata tac cag tat att cag agt cgc ttt tat cgg tct   1062
```

-continued

| | | |
|---|---|---|
| Leu Gly Gln Arg Ile Tyr Gln Tyr Ile Gln Ser Arg Phe Tyr Arg Ser<br>315               320                   325 | | |
| cca gag gtg cta ctg gga atg cct tat gac ctt gcc att gat atg tgg<br>Pro Glu Val Leu Leu Gly Met Pro Tyr Asp Leu Ala Ile Asp Met Trp<br>330               335              340              345 | 1110 |
| tcc ctc ggg tgt att ttg gtt gaa atg cac act gga gaa cct ctg ttc<br>Ser Leu Gly Cys Ile Leu Val Glu Met His Thr Gly Glu Pro Leu Phe<br>               350                    355                    360 | 1158 |
| agt ggt gcc aat gag gta gat cag atg aat aaa ata gtg gaa gtt ctg<br>Ser Gly Ala Asn Glu Val Asp Gln Met Asn Lys Ile Val Glu Val Leu<br>               365                    370                   375 | 1206 |
| ggt att cca cct gct cat att ctt gac caa gca cca aaa gca aga aag<br>Gly Ile Pro Pro Ala His Ile Leu Asp Gln Ala Pro Lys Ala Arg Lys<br>380               385                   390 | 1254 |
| ttc ttt gag aag ttg cca gat ggc act tgg aac tta aag aag acc aaa<br>Phe Phe Glu Lys Leu Pro Asp Gly Thr Trp Asn Leu Lys Lys Thr Lys<br>395               400              405 | 1302 |
| gat gga aaa cgg gag tac aaa cca cca gga acc cgt aaa ctt cat aac<br>Asp Gly Lys Arg Glu Tyr Lys Pro Pro Gly Thr Arg Lys Leu His Asn<br>410               415                   420              425 | 1350 |
| att ctt gga gtg gaa aca gga gga cct ggt ggg cga cgt gct ggg gag<br>Ile Leu Gly Val Glu Thr Gly Gly Pro Gly Gly Arg Arg Ala Gly Glu<br>               430                    435                   440 | 1398 |
| tca ggt cat acg gtc gct gac tac ttg aag ttc aaa gac ctc att tta<br>Ser Gly His Thr Val Ala Asp Tyr Leu Lys Phe Lys Asp Leu Ile Leu<br>               445                    450                   455 | 1446 |
| agg atg ctt gat tat gac ccc aaa act cga att caa cct tat tat gct<br>Arg Met Leu Asp Tyr Asp Pro Lys Thr Arg Ile Gln Pro Tyr Tyr Ala<br>               460                    465                   470 | 1494 |
| ctg cag cac agt ttc ttc aag aaa aca gct gat gaa ggt aca aat aca<br>Leu Gln His Ser Phe Phe Lys Lys Thr Ala Asp Glu Gly Thr Asn Thr<br>475               480              485 | 1542 |
| agt aat agt gta tct aca agc ccc gcc atg gag cag tct cag tct tcg<br>Ser Asn Ser Val Ser Thr Ser Pro Ala Met Glu Gln Ser Gln Ser Ser<br>490               495                   500              505 | 1590 |
| ggc acc acc tcc agt aca tcg tca agc tca ggt ggc tca tcg ggg aca<br>Gly Thr Thr Ser Ser Thr Ser Ser Ser Ser Gly Gly Ser Ser Gly Thr<br>               510                    515                   520 | 1638 |
| agc aac agt ggg aga gcc cgg tcg gat ccg acg cac cag cat cgg cac<br>Ser Asn Ser Gly Arg Ala Arg Ser Asp Pro Thr His Gln His Arg His<br>               525                    530                   535 | 1686 |
| agt ggt ggg cac ttc aca gct gcc gtg cag gcc atg gac tgc gag aca<br>Ser Gly Gly His Phe Thr Ala Ala Val Gln Ala Met Asp Cys Glu Thr<br>               540                    545                   550 | 1734 |
| cac agt ccc cag gtg cgt cag caa ttt cct gct cct ctt ggt tgg tca<br>His Ser Pro Gln Val Arg Gln Gln Phe Pro Ala Pro Leu Gly Trp Ser<br>555               560              565 | 1782 |
| ggc act gaa gct cct aca cag gtc act gtt gaa act cat cct gtt caa<br>Gly Thr Glu Ala Pro Thr Gln Val Thr Val Glu Thr His Pro Val Gln<br>570               575              580              585 | 1830 |
| gaa aca acc ttt cat gta gcc cct caa cag aat gca ttg cat cat cac<br>Glu Thr Thr Phe His Val Ala Pro Gln Gln Asn Ala Leu His His His<br>               590                    595                   600 | 1878 |
| cat ggt aac agt tcc cat cat cac cac cac cac cac cac cat cac cac<br>His Gly Asn Ser Ser His His His His His His His His His His His<br>               605                    610                   615 | 1926 |
| cac cat gga caa caa gcc ttg ggt aac cgg acc agg cca agg gtc tac<br>His His Gly Gln Gln Ala Leu Gly Asn Arg Thr Arg Pro Arg Val Tyr<br>               620                    625                   630 | 1974 |

-continued

| | | |
|---|---|---|
| aat tct cca acg aat agc tcc tct acc caa gat tct atg gag gtt ggc<br>Pro Thr Asn Ser Ser Thr Gln Asp Ser Met Glu Val Gly Asn Ser<br>635                   640                 645 | | 2022 |
| cac agt cac cac tcc atg aca tcc ctg tct tcc tca acg act tct tcc<br>His Ser His His Ser Met Thr Ser Leu Ser Ser Ser Thr Thr Ser Ser<br>650                   655                 660                 665 | | 2070 |
| tcg aca tct tcc tcc tct act ggt aac caa ggc aat cag gcc tac cac<br>Ser Thr Ser Ser Ser Thr Gly Asn Gln Gly Asn Gln Ala Tyr His<br>                670                 675                 680 | | 2118 |
| aat cgc cca gtg gct gct aat acc ttg gac ttt gga cag aat gga gct<br>Asn Arg Pro Val Ala Ala Asn Thr Leu Asp Phe Gly Gln Asn Gly Ala<br>                685                 690                 695 | | 2166 |
| atg gac gtt aat ttg acc gtc tac tcc aat ccc cgc caa gag act ggc<br>Met Asp Val Asn Leu Thr Val Tyr Ser Asn Pro Arg Gln Glu Thr Gly<br>                700                 705                 710 | | 2214 |
| ata gct gga cat cca aca tac caa ttt tct gct aat aca ggt cct gca<br>Ile Ala Gly His Pro Thr Tyr Gln Phe Ser Ala Asn Thr Gly Pro Ala<br>715                   720                 725 | | 2262 |
| cat tac atg act gaa gga cat ctg acg atg agg caa ggg gct gat aga<br>His Leu Thr Met Arg Gln Gly Ala Asp Lys Glu Glu Ser Pro Met Arg<br>730                   735                 740                 745 | | 2310 |
| gaa gag tcc ccc atg aca gga gtt tgt gtg caa cag agt cct gta gct<br>Gly His Tyr Met Thr Glu Gly Val Cys Val Gln Gln Ser Pro Val Ala<br>                750                 755                 760 | | 2358 |
| agc tcg tga ctacat<br>Ser Ser | | 2373 |

<210> SEQ ID NO: 2
<211> LENGTH: 20
<212> TYPE: DNA
<213> ORGANISM: Artificial sequence
<220> FEATURE:
<223> OTHER INFORMATION: To link cDNAs

<400> SEQUENCE: 2
ctcgagaatt ctggatcctc                                                        20

<210> SEQ ID NO: 3
<211> LENGTH: 40
<212> TYPE: DNA
<213> ORGANISM: Homo sapiens
<220> FEATURE:

<400> SEQUENCE: 3
ggaataccca gaacttccac tattttattc atctgatcta                        40

<210> SEQ ID NO; 4
<211> LENGTH: 763
<212> TYPE: PRT
<213> ORGANISM: Homo sapiens
<220> FEATURE:

<400> SEQUENCE: 4

Met His Thr Gly Gly Glu Thr Ser Ala Cys Lys Pro Ser Ser Val Arg
                5                         10                       15

Leu Ala Pro Ser Phe Ser Phe His Ala Ala Gly Leu Gln Met Ala Gly
                20                         25                       30

Gln Met Pro His Ser His Gln Tyr Ser Asp Arg Arg Gln Pro Asn Ile
                35                         40                       45

Ser Asp Gln Gln Val Ser Ala Leu Ser Tyr Ser Asp Gln Ile Gln Gln
                50                         55                       60

-continued

```
Pro Leu Thr Asn Gln Val Met Pro Asp Ile Val Met Leu Gln Arg Arg
 65                  70                  75                  80

Met Pro Gln Thr Phe Arg Asp Pro Ala Thr Ala Pro Leu Arg Lys Leu
                 85                  90                  95

Ser Val Asp Leu Ile Lys Thr Tyr Lys His Ile Asn Glu Val Tyr Tyr
            100                 105                 110

Ala Lys Lys Arg Arg His Gln Gln Gly Gln Gly Asp Asp Ser Ser
            115                 120                 125

His Lys Lys Glu Arg Lys Val Tyr Asn Asp Gly Tyr Asp Asp Asp Asn
    130                 135                 140

Tyr Asp Tyr Ile Val Lys Asn Gly Glu Lys Trp Met Asp Arg Tyr Glu
145                 150                 155                 160

Ile Asp Ser Leu Ile Gly Lys Gly Ser Phe Gly Gln Val Val Lys Ala
                165                 170                 175

Tyr Asp Arg Val Glu Gln Glu Trp Val Ala Ile Lys Ile Ile Lys Asn
            180                 185                 190

Lys Lys Ala Phe Leu Asn Gln Ala Gln Ile Glu Val Arg Leu Leu Glu
            195                 200                 205

Leu Met Asn Lys His Asp Thr Glu Met Lys Tyr Tyr Ile Val His Leu
210                 215                 220

Lys Arg His Phe Met Phe Arg Asn His Leu Cys Leu Val Phe Glu Met
225                 230                 235                 240

Leu Ser Tyr Asn Leu Tyr Asp Leu Leu Arg Asn Thr Asn Phe Arg Gly
                245                 250                 255

Val Ser Leu Asn Leu Thr Arg Lys Phe Ala Gln Gln Met Cys Thr Ala
            260                 265                 270

Leu Leu Phe Leu Ala Thr Pro Glu Leu Ser Ile Ile His Cys Asp Leu
            275                 280                 285

Lys Pro Glu Asn Ile Leu Leu Cys Asn Pro Lys Arg Ser Ala Ile Lys
290                 295                 300

Ile Val Asp Phe Gly Ser Ser Cys Gln Leu Gly Gln Arg Ile Tyr Gln
305                 310                 315                 320

Tyr Ile Gln Ser Arg Phe Tyr Arg Ser Pro Glu Val Leu Leu Gly Met
                325                 330                 335

Pro Tyr Asp Leu Ala Ile Asp Met Trp Ser Leu Gly Cys Ile Leu Val
            340                 345                 350

Glu Met His Thr Gly Glu Pro Leu Phe Ser Gly Ala Asn Glu Val Asp
            355                 360                 365

Gln Met Asn Lys Ile Val Glu Val Leu Gly Ile Pro Pro Ala His Ile
    370                 375                 380

Leu Asp Gln Ala Pro Lys Ala Arg Lys Phe Phe Glu Lys Leu Pro Asp
385                 390                 395                 400

Gly Thr Trp Asn Leu Lys Lys Thr Lys Asp Gly Lys Arg Glu Tyr Lys
                405                 410                 415

Pro Pro Gly Thr Arg Lys Leu His Asn Ile Leu Gly Val Glu Thr Gly
            420                 425                 430

Gly Pro Gly Gly Arg Arg Ala Gly Glu Ser Gly His Thr Val Ala Asp
            435                 440                 445

Tyr Leu Lys Phe Lys Asp Leu Ile Leu Arg Met Leu Asp Tyr Asp Pro
    450                 455                 460

Lys Thr Arg Ile Gln Pro Tyr Tyr Ala Leu Gln His Ser Phe Phe Lys
465                 470                 475                 480

Lys Thr Ala Asp Glu Gly Thr Asn Thr Ser Asn Ser Val Ser Thr Ser
```

-continued

```
                    485                 490                     495
Pro Ala Met Glu Gln Ser Gln Ser Ser Gly Thr Thr Ser Ser Thr Ser
                500                 505                 510

Ser Ser Ser Gly Gly Ser Ser Gly Thr Ser Asn Ser Gly Arg Ala Arg
            515                 520                 525

Ser Asp Pro Thr His Gln His Arg His Ser Gly Gly His Phe Thr Ala
        530                 535                 540

Ala Val Gln Ala Met Asp Cys Glu Thr His Ser Pro Gln Val Arg Gln
545                 550                 555                 560

Gln Phe Pro Ala Pro Leu Gly Trp Ser Gly Thr Glu Ala Pro Thr Gln
                565                 570                 575

Val Thr Val Glu Thr His Pro Val Gln Glu Thr Thr Phe His Val Ala
                580                 585                 590

Pro Gln Gln Asn Ala Leu His His His Gly Asn Ser Ser His His
            595                 600                 605

His His His His His His His His His Gly Gln Gln Ala Leu
        610                 615                 620

Gly Asn Arg Thr Arg Pro Arg Val Tyr Asn Ser Pro Thr Asn Ser Ser
625                 630                 635                 640

Ser Thr Gln Asp Ser Met Glu Val Gly His Ser His His Ser Met Thr
                645                 650                 655

Ser Leu Ser Ser Ser Thr Thr Ser Ser Thr Ser Ser Ser Ser Thr
                660                 665                 670

Gly Asn Gln Gly Asn Gln Ala Tyr His Asn Arg Pro Val Ala Ala Asn
            675                 680                 685

Thr Leu Asp Phe Gly Gln Asn Gly Ala Met Asp Val Asn Leu Thr Val
        690                 695                 700

Tyr Ser Asn Pro Arg Gln Glu Thr Gly Ile Ala Gly His Pro Thr Tyr
705                 710                 715                 720

Gln Phe Ser Ala Asn Thr Gly Pro Ala His Tyr Met Thr Glu Gly His
                725                 730                 735

Leu Thr Met Arg Gln Gly Ala Asp Arg Glu Glu Ser Pro Met Thr Gly
                740                 745                 750

Val Cys Val Gln Gln Ser Pro Val Ala Ser Ser
            755                 760

<210> SEQ ID NO: 5
<211> LENGTH: 763
<212> TYPE: PRT
<213> ORGANISM: Rat norvegicus
<220> FEATURE:

<400> SEQUENCE: 5

Met His Thr Gly Gly Glu Thr Ser Ala Cys Lys Pro Ser Ser Val Arg
                5                   10                  15

Leu Ala Pro Ser Phe Ser Phe His Ala Ala Gly Leu Gln Met Ala Ala
            20                  25                  30

Gln Met Pro His Ser His Gln Tyr Ser Asp Arg Arg Gln Pro Asn Ile
        35                  40                  45

Ser Asp Gln Gln Val Ser Ala Leu Ser Tyr Ser Asp Gln Ile Gln Gln
    50                  55                  60

Pro Leu Thr Asn Gln Val Met Pro Asp Ile Val Met Leu Gln Arg Arg
65                  70                  75                  80

Met Pro Gln Thr Phe Arg Asp Pro Ala Thr Ala Pro Leu Arg Lys Leu
                85                  90                  95
```

-continued

```
Ser Val Asp Leu Ile Lys Thr Tyr Lys His Ile Asn Glu Val Tyr Tyr
            100                 105                 110
Ala Lys Lys Lys Arg Arg His Gln Gln Gly Gln Gly Asp Asp Ser Ser
        115                 120                 125
His Lys Lys Glu Arg Lys Val Tyr Asn Asp Gly Tyr Asp Asp Asp Asn
    130                 135                 140
Tyr Asp Tyr Ile Val Lys Asn Gly Glu Lys Trp Met Asp Arg Tyr Glu
145                 150                 155                 160
Ile Asp Ser Leu Ile Gly Lys Gly Ser Phe Gly Gln Val Val Lys Ala
                165                 170                 175
Tyr Asp Arg Val Glu Gln Glu Trp Val Ala Ile Lys Ile Ile Lys Asn
            180                 185                 190
Lys Lys Ala Phe Leu Asn Gln Ala Gln Ile Glu Val Arg Leu Leu Glu
        195                 200                 205
Leu Met Asn Lys His Asp Thr Glu Met Lys Tyr Tyr Ile Val His Leu
    210                 215                 220
Lys Arg His Phe Met Phe Arg Asn His Leu Cys Leu Val Phe Glu Met
225                 230                 235                 240
Leu Ser Tyr Asn Leu Tyr Asp Leu Leu Arg Asn Thr Asn Phe Arg Gly
                245                 250                 255
Val Ser Leu Asn Leu Thr Arg Lys Phe Ala Gln Gln Met Cys Thr Ala
            260                 265                 270
Leu Leu Phe Leu Ala Thr Pro Glu Leu Ser Ile Ile His Cys Asp Leu
        275                 280                 285
Lys Pro Glu Asn Ile Leu Leu Cys Asn Pro Lys Arg Ser Ala Ile Lys
    290                 295                 300
Ile Val Asp Phe Gly Ser Ser Cys Gln Leu Gly Gln Arg Ile Tyr Gln
305                 310                 315                 320
Tyr Ile Gln Ser Arg Phe Tyr Arg Ser Pro Glu Val Leu Leu Gly Met
                325                 330                 335
Pro Tyr Asp Leu Ala Ile Asp Met Trp Ser Leu Gly Cys Ile Leu Val
            340                 345                 350
Glu Met His Thr Gly Glu Pro Leu Phe Ser Gly Ala Asn Glu Val Asp
        355                 360                 365
Gln Met Asn Lys Ile Val Glu Val Leu Gly Ile Pro Pro Ala His Ile
    370                 375                 380
Leu Asp Gln Ala Pro Lys Ala Arg Lys Phe Phe Glu Lys Leu Pro Asp
385                 390                 395                 400
Gly Thr Trp Ser Leu Lys Lys Thr Lys Asp Gly Lys Arg Glu Tyr Lys
                405                 410                 415
Pro Pro Gly Thr Arg Lys Leu His Asn Ile Leu Gly Val Glu Thr Gly
            420                 425                 430
Gly Pro Gly Gly Arg Arg Ala Gly Glu Ser Gly His Thr Val Ala Asp
        435                 440                 445
Tyr Leu Lys Phe Lys Asp Leu Ile Leu Arg Met Leu Asp Tyr Asp Pro
    450                 455                 460
Lys Thr Arg Ile Gln Pro Tyr Tyr Ala Leu Gln His Ser Phe Phe Lys
465                 470                 475                 480
Lys Thr Ala Asp Glu Gly Thr Asn Thr Ser Asn Ser Val Ser Thr Ser
                485                 490                 495
Pro Ala Met Glu Gln Ser Gln Ser Ser Gly Thr Thr Ser Ser Thr Ser
            500                 505                 510
```

-continued

```
Ser Ser Ser Gly Gly Ser Ser Gly Thr Ser Asn Ser Gly Arg Ala Arg
        515                 520                 525

Ser Asp Pro Thr His Gln His Arg His Ser Gly Gly His Phe Ala Ala
        530                 535                 540

Ala Val Gln Ala Met Asp Cys Glu Thr His Ser Pro Gln Val Arg Gln
545                 550                 555                 560

Gln Phe Pro Ala Pro Leu Gly Trp Ser Gly Thr Glu Ala Pro Thr Gln
                565                 570                 575

Val Thr Val Glu Thr His Pro Val Gln Glu Thr Thr Phe His Val Ala
            580                 585                 590

Pro Gln Gln Asn Ala Leu His His His Gly Asn Ser Ser His His
        595                 600                 605

His His His His His His His His His Gly Gln Gln Ala Leu
        610                 615                 620

Gly Asn Arg Thr Arg Pro Arg Val Tyr Asn Ser Pro Thr Asn Ser Ser
625                 630                 635                 640

Ser Thr Gln Asp Ser Met Glu Val Gly His Ser His His Ser Met Thr
                645                 650                 655

Ser Leu Ser Ser Ser Thr Thr Ser Ser Ser Thr Ser Ser Ser Ser Thr
                660                 665                 670

Gly Asn Gln Gly Asn Gln Ala Tyr Gln Asn Arg Pro Val Ala Ala Asn
                675                 680                 685

Thr Leu Asp Phe Gly Gln Asn Gly Ala Met Asp Val Asn Leu Tyr Val
        690                 695                 700

Tyr Ser Asn Pro Arg Gln Glu Thr Ala Ile Ala Gly His Pro Thr Tyr
705                 710                 715                 720

Gln Phe Ser Ala Asn Thr Gly Pro Ala His Tyr Met Thr Glu Gly His
                725                 730                 735

Leu Thr Met Arg Gln Gly Ala Asp Arg Glu Ser Pro Met Thr Gly
                740                 745                 750

Val Cys Val Gln Gln Ser Pro Val Ala Ser Ser
        755                 760
```

<210> SEQ ID NO: 6
<211> LENGTH: 539
<212> TYPE: PRT
<213> ORGANISM: Drosophila melanogaster
<220> FEATURE:

<400> SEQUENCE: 6

```
Met His His His Ser Ser Pro Ser Ser Ser Glu Val Arg Ala Met
                5                   10                  15

Gln Ala Arg Ile Pro Asn His Phe Arg Glu Pro Ala Ser Gly Pro Leu
            20                  25                  30

Arg Lys Leu Ser Val Asp Leu Ile Lys Thr Tyr Lys His Ile Asn Glu
        35                  40                  45

Val Tyr Tyr Ala Lys Lys Lys Arg Arg Ala Gln Gln Thr Gln Gly Asp
    50                  55                  60

Asp Asp Ser Ser Asn Lys Lys Glu Arg Lys Leu Tyr Asn Asp Gly Tyr
65                  70                  75                  80

Asp Asp Asp Asn His Asp Tyr Ile Ile Lys Asn Gly Glu Lys Phe Leu
                85                  90                  95

Asp Arg Tyr Glu Ile Asp Ser Leu Ile Gly Lys Gly Ser Phe Gly Gln
            100                 105                 110

Val Val Lys Ala Tyr Asp His Glu Glu Gln Cys His Val Ala Ile Lys
```

-continued

```
                115                 120                 125
Ile Ile Lys Asn Lys Lys Pro Phe Leu Asn Gln Ala Gln Ile Glu Val
        130                 135                 140
Lys Leu Leu Glu Met Met Asn Arg Ala Asp Ala Glu Asn Lys Tyr Tyr
145                 150                 155                 160
Ile Val Lys Leu Lys Arg His Phe Met Trp Arg Asn His Leu Cys Leu
                165                 170                 175
Val Phe Glu Leu Leu Ser Tyr Asn Leu Tyr Asp Leu Leu Arg Asn Thr
                180                 185                 190
Asn Phe Arg Gly Val Ser Leu Asn Leu Thr Arg Lys Phe Ala Gln Gln
                195                 200                 205
Leu Cys Thr Ala Leu Leu Phe Leu Ser Thr Pro Glu Leu Asn Ile Ile
210                 215                 220
His Cys Asp Leu Lys Pro Glu Asn Ile Leu Leu Cys Asn Pro Lys Arg
225                 230                 235                 240
Ser Ala Ile Lys Ile Val Asp Phe Gly Ser Ser Cys Gln Leu Gly Gln
                245                 250                 255
Arg Ile Tyr His Tyr Ile Gln Ser Arg Phe Tyr Arg Ser Pro Glu Val
                260                 265                 270
Leu Leu Gly Ile Gln Tyr Asp Leu Ala Ile Asp Met Trp Ser Leu Gly
                275                 280                 285
Cys Ile Leu Val Glu Met His Thr Gly Glu Pro Leu Phe Ser Gly Cys
        290                 295                 300
Asn Glu Val Asp Gln Met Asn Lys Ile Val Glu Val Leu Gly Met Pro
305                 310                 315                 320
Pro Lys Tyr Leu Leu Asp Gln Ala His Lys Thr Arg Lys Phe Phe Asp
                325                 330                 335
Lys Ile Val Ala Asp Gly Ser Tyr Val Leu Lys Lys Asn Gln Asn Gly
                340                 345                 350
Arg Lys Tyr Lys Pro Pro Gly Ser Arg Lys Leu His Asp Ile Leu Gly
                355                 360                 365
Val Glu Thr Gly Gly Pro Gly Gly Arg Arg Leu Asp Glu Pro Gly His
        370                 375                 380
Ser Val Ser Asp Tyr Leu Lys Phe Lys Asp Leu Ile Leu Arg Met Leu
385                 390                 395                 400
Asp Phe Asp Pro Lys Thr Arg Val Thr Pro Tyr Tyr Ala Leu Gln His
                405                 410                 415
Asn Phe Phe Lys Arg Thr Ala Asp Glu Ala Thr Asn Thr Ser Gly Ala
                420                 425                 430
Gly Ala Thr Ala Asn Ala Gly Ala Gly Ser Gly Ser Ser Gly Ala
                435                 440                 445
Gly Gly Ser Ser Gly Gly Val Gly Gly Leu Gly Ala Ser Asn
        450                 455                 460
Ser Ser Ser Gly Ala Val Ser Ser Ser Ala Ala Pro Thr Ala
465                 470                 475                 480
Ala Thr Ala Ala Thr Ala Ala Gly Ser Ser Gly Ser Gly Ser Ser
                485                 490                 495
Val Gly Gly Gly Ser Ser Ala Ala Gln Gln Gln Gln Ala Met Pro Leu
        500                 505                 510
```

```
Pro Leu Pro Leu Pro Leu Pro Leu Pro Pro Leu Ala Gly Pro Gly Gly
        515                 520                 525

Ala Ser Asp Gly Gln Cys His Asp Asp Arg Arg
    530                 535
```

What is claimed is:

1. An isolated human Down Syndrome critical region (MNB) DNA sequence consisting of the nucleotide sequence depicted in SEQ ID NO:1.

2. A vector comprising the human Down Syndrome critical region (MNB) DNA sequence of claim 1.

3. Isolated host cells comprising the vector of claim 2.

* * * * *